United States Patent
Baek et al.

(10) Patent No.: US 11,697,810 B2
(45) Date of Patent: Jul. 11, 2023

(54) ADENYLOSUCCINATE SYNTHETASE AND METHOD FOR PRODUCING PURINE NUCLEOTIDES USING THE SAME

(71) Applicant: CJ CHEILJEDANG CORPORATION, Seoul (KR)

(72) Inventors: Min Ji Baek, Suwon-si (KR); Ji Hye Lee, Anyang-si (KR); So-Jung Park, Suwon-si (KR); Jee Yeon Bae, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 14 days.

(21) Appl. No.: 17/551,890

(22) Filed: Dec. 15, 2021

(65) Prior Publication Data

US 2022/0098569 A1 Mar. 31, 2022

Related U.S. Application Data

(62) Division of application No. 16/482,615, filed as application No. PCT/KR2018/009714 on Aug. 23, 2018, now Pat. No. 11,236,321.

(30) Foreign Application Priority Data

Aug. 1, 2018 (KR) ........................ 10-2018-0089855

(51) Int. Cl.
C12N 9/00 (2006.01)
C12N 15/52 (2006.01)
C12N 15/77 (2006.01)

(52) U.S. Cl.
CPC ............... *C12N 9/93* (2013.01); *C12N 15/52* (2013.01); *C12N 15/77* (2013.01); *C12Y 603/04004* (2013.01)

(58) Field of Classification Search
CPC .......... C12N 9/93; C12N 15/52; C12N 15/77; C12Y 603/04004
See application file for complete search history.

(56) References Cited

FOREIGN PATENT DOCUMENTS

| CN | 103952419 B | 6/2016 |
|----|----|----|
| JP | 2012-29678 A | 2/2012 |
| KR | 10-2010-0109732 A | 10/2010 |

OTHER PUBLICATIONS

Asahara et al., "Accumulation of gene-targeted *Bacillus subtilis* mutations that enhance fermentative inosine production," *Appl Microbiol Biotechnol* 87:2195-2207 (2010).
NCBI Reference Sequence WP_075723579.1, adenylosuccinate synthase [Corynebacterium stationis] (1 page) (Jan. 12, 2017).
Ledesma-Amaro et al., "Increased production of inosine and guanosine by means of metabolic engineering of the purine pathway in *Ashbya gossypii*," *Microbial Cell Factories* 14:58 (8 pages) (2015).
Mehrotra et al., "Studies on active site mutants of *P. falciparum* adenylosuccinate synthetase: Insights into enzyme catalysis and activation," *Biochimica et Biophysica Acta* 1804:1996-2002 (2010).
Peifer et al., "Metabolic engineering of the purine biosynthetic pathway in *Corynebacterium glutamicum* results in increased intracellular pool sizes of IMP and hypoxanthine," *Microbial Cell Factories* 11:138, 14 pages (2012).
Qian et al., "Nucleotide mutations in purA gene and pur operon promoter discovered in guanosine- and inosine-producing *Bacillus subtilis* strains," *Biotechnol Letters* 28(12):937-941 (2006).
UniProtKB—A4QHG2 (PURA_CORGB), 7 pages (2007).
Wang et al., "Directed evolution of adenylosuccinate synthetase from *Bacillus subtilis* and its application in metabolic engineering," *Journal of Biotechnology* 231:115-121 (2016).
Xu et al., "Improvement of the riboflavin production by engineering the precursor biosynthesis pathways in *Escherichia coli*," *Chinese Journal of Chemical Engineering* 23:1834-1839 (2015).
UniProtKB—A9WV79 (PURA_RENSM), 8 pages (2008).
UniProtKB—D4YN81 (D4YN81_9MICO), 7 pages (2010).

*Primary Examiner* — Paul J Holland
(74) *Attorney, Agent, or Firm* — Seed IP Law Group LLP

(57) ABSTRACT

The present disclosure relates to an adenylosuccinate synthetase variant, a microorganism containing the same, and a method for preparing purine nucleotides using the microorganism.

10 Claims, No Drawings

Specification includes a Sequence Listing.

ADENYLOSUCCINATE SYNTHETASE AND METHOD FOR PRODUCING PURINE NUCLEOTIDES USING THE SAME

CROSS REFERENCE TO RELATED APPLICATIONS

The present application is a divisional application of U.S. application Ser. No. 16/482,615 filed Jul. 31, 2019, now pending, which is a U.S. national phase application of PCT/KR2018/009714, filed Aug. 23, 2018, which claims priority to KR Application No. 10-2018-0089855, filed Aug. 1, 2018. U.S. application Ser. No. 16/482,615 is herein incorporated by reference in its entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_446D1_SEQUENCE_LISTING.txt. The text file is 19 KB, was created on Dec. 13, 2021, and is being submitted electronically via EFS-Web.

TECHNICAL FIELD

The present disclosure relates to a novel adenylosuccinate synthetase, a microorganism containing the same, and a method for preparing purine nucleotides using the microorganism.

BACKGROUND ART

5'-Inosine monophosphate (hereinafter, IMP), a nucleic acid-based material, is an intermediate of the nucleic acid biosynthetic metabolic system used in various fields (e.g., medicines, various medical applications, etc.), and is a material widely used as a food seasoning additive or food along with 5'-guanine monophosphate (hereinafter, GMP). It is known that IMP itself produces a beef flavor and enhances the flavor of monosodium glutamic acid (MSG) like GMP, thus attracting public attention as a taste-based nucleic acid-based seasoning.

Methods of preparing IMP may include a method of enzymatically degrading ribonucleic acid extracted from yeast cells, a method of chemically phosphorylating inosine produced by fermentation (*Agri. Biol. Chem.*, 36, 1511 (1972), etc.), a method of culturing a microorganism that directly produces IMP and recovering IMP from the cultured medium, etc. Among these methods, the most widely used method is that of using a microorganism capable of directly producing IMP.

Additionally, the method of preparing GMP may include a method of converting xanthosine 5'-monophosphate (hereinafter, XMP) produced by microbial fermentation into GMP using a coryneform microorganism and a method of converting XMP produced by microbial fermentation into GMP using *Escherichia coli*. In the above methods, when GMP is produced by a method where XMP is produced first and then converted into GMP, the productivity of XMP (i.e., a precursor of the conversion reaction during the microbial fermentation) must be enhanced, and additionally, both the produced XMP and the GMP already produced during the entire process of the conversion reaction should be protected from being lost.

Meanwhile, since enzymes in nature do not always exhibit optimal properties in terms of activity, stability, substrate specificity to optical isomers, etc. in industrial applications, various attempts have been made to improve enzymes to achieve the desired use by variation of their amino acid sequences. Among these, rational design and site-directed mutagenesis of enzymes have been applied to improve functions of enzymes in some cases; however, these methods have disadvantages in that information on the structure of the target enzyme is not sufficient or the structure-function correlation is not clear, and thus they cannot be effectively applied. In this case, it has been reported that the activity of an enzyme can be enhanced by improving the enzyme through a directed evolution method, in which enzymes of the desired traits are screened from a mutant library of enzymes constructed through random variations of enzyme genes. The inventors of the present disclosure have performed extensive research for high-yield production of purine nucleotides by a method producing purine nucleotides containing IMP or XMP through the microbial fermentation. As a result, they have discovered protein variants having higher productivity of purine nucleotides, thereby completing the present disclosure.

DISCLOSURE

Technical Problem

An object of the present disclosure is to provide an adenylosuccinate synthetase variant.

Another object of the present disclosure is to provide a polynucleotide encoding the adenylosuccinate synthetase variant.

Still another object of the present disclosure is to provide a vector containing the polynucleotide.

Still another object of the present disclosure is to provide a microorganism capable of producing purine nucleotides, which contains the adenylosuccinate synthetase variant and the vector.

Still another object of the present disclosure is to provide a method for preparing purine nucleotides, which includes culturing the microorganism of the genus *Corynebacterium* in a medium; and recovering the purine nucleotides from the microorganism or the medium.

Technical Solution

Hereinbelow, exemplary embodiments of the present disclosure will be described in detail. Meanwhile, each of the explanations and exemplary embodiments disclosed herein can be applied to other explanations and exemplary embodiments. That is, all of the combinations of various factors disclosed herein belong to the scope of the present disclosure. Furthermore, the scope of the present disclosure should not be limited by the specific disclosure provided hereinbelow.

To achieve the above objects, an aspect of the present disclosure provides an adenylosuccinate synthetase variant in which the $85^{th}$ amino acid from the N-terminus of the amino acid sequence of SEQ ID NO: 2 is substituted with a different amino acid. The modified adenylosuccinate synthetase has a modification on the amino acid at the $85^{th}$ position from the N-terminus of the amino acid sequence of SEQ ID NO: 2. Specifically, the present disclosure provides an adenylosuccinate synthetase variant having at least one amino acid variation in the amino acid sequence of SEQ ID NO: 2, in which the modification includes a substitution of the 85th position from the N-terminus with a different amino acid.

As used herein, the term "adenylosuccinate synthetase" refers to an enzyme having an important role in purine biosynthesis. For the purpose of the present disclosure, the enzyme refers to a protein involved in the production of purine nucleotides including 5'-inosine monophosphate (IMP) or 5'-xanthosine monophosphate (XMP).

In the present disclosure, SEQ ID NO: 2 refers to an amino acid sequence having the activity of adenylosuccinate synthetase. Specifically, SEQ ID NO: 2 is a protein sequence having the activity of adenylosuccinate synthetase encoded by purA gene. The amino acid sequence of SEQ ID NO: 2 may be obtained from NCBI GenBank, which is a known database. In an embodiment, the amino acid sequence of SEQ ID NO: 2 may be derived from a microorganism of the genus Corynebacterium, but is not limited thereto, and may include any sequence having the same activity as the above amino acid sequence without limitation. Additionally, the scope of the amino acid sequence of SEQ ID NO: 2 may include the amino acid sequence of SEQ ID NO: 2 having the activity of adenylosuccinate synthetase or an amino acid sequence having 80% or more homology or identity to the amino acid sequence of SEQ ID NO: 2, but is not limited thereto. Specifically, the above amino acid sequence may include the amino acid sequence of SEQ ID NO: 2 and/or an amino acid sequence having at least 80%, 85%, 90%, 95%, 96%, 97%, 98%, or 99% or more homology or identity to the amino acid sequence of SEQ ID NO: 2. The amino acid sequence having homology or identity may be those in the above range, excluding a sequence having 100% identity, or may be a sequence having less than 100% identity. Additionally, it is apparent that any protein having an amino acid sequence having deletion, modification, substitution, or addition in part of the sequence can also be used in the present disclosure as long as it has the homology or identity and exhibits efficacy corresponding to that of the above protein.

In the present disclosure, the term "adenylosuccinate synthetase variant" may be used interchangeably with a polypeptide variant having purine nucleotide productivity, a purine nucleotide-producing variant polypeptide, a polypeptide variant producing purine nucleotides, a polypeptide variant having the adenylosuccinate synthetase activity, an adenylosuccinate synthetase variant, etc. Additionally, the protein may be derived from the genus Corynebacterium stationis, but the protein is not limited thereto.

The adenylosuccinate synthetase variant includes a modification of the amino acid at the 85th position from the N-terminus in the amino acid sequence of SEQ ID NO: 2. The adenylosuccinate synthetase variant is that where the 85th amino acid in the amino acid sequence of SEQ ID NO: 2 is substituted with a different amino acid. The adenylosuccinate synthetase variant may include the amino acid sequence of SEQ ID NO: 2 or it may be an adenylosuccinate synthetase variant having weaker activity compared to a non-variant adenylosuccinate synthetase derived from a wild-type microorganism. Such an adenylosuccinate synthetase variant indicates the modification of the 85th amino acid from the N-terminus in the amino acid sequence of SEQ ID NO: 2 or the amino acid sequence having at least 80%, 85%, 90%, 95%, 96%, 97%, 98%, or 99% or more homology or identity to the amino acid sequence of SEQ ID NO: 2, as explained above.

Specifically, the adenylosuccinate synthetase variant is that where the 85th amino acid in the amino acid sequence of SEQ ID NO: 2 is substituted with serine, alanine, valine, leucine, methionine, isoleucine, threonine, asparagine, glutamine, cysteine, tyrosine, lysine, aspartic acid, or glutamic acid, and the adenylosuccinate synthetase variant may have weaker activity of adenylosuccinate synthetase compared to that of a polypeptide including the amino acid sequence of SEQ ID NO: 2, but the adenylosuccinate synthetase variant is not limited thereto.

For the purpose of the present disclosure, when a microorganism includes the adenylosuccinate synthetase variant, the amount of purine nucleotide production including IMP or XMP is increased. This is meaningful in that the present disclosure enables the increase of the amount of IMP or XMP production through the adenylosuccinate synthetase variant of the present disclosure while the wild-type Corynebacterium strain cannot produce IMP or XMP, or can only produce a very small amount even if IMP or XMP is produced.

The adenylosuccinate synthetase variant may include an amino acid sequence selected from the group of amino acid sequences where the 85th amino acid from the N-terminus in the amino acid sequence of SEQ ID NO: 2 is substituted with an amino acid selected from the group consisting of serine, alanine, valine, leucine, methionine, isoleucine, threonine, asparagine, glutamine, cysteine, tyrosine, lysine, aspartic acid, and glutamic acid.

Specifically, the adenylosuccinate synthetase variant may be comprised of a polypeptide including an amino acid sequence, which is selected from the group of amino acid sequences where the 85th amino acid from the N-terminus in the amino acid sequence of SEQ ID NO: 2 is substituted with an amino acid selected from the group consisting of serine, alanine, valine, leucine, methionine, isoleucine, threonine, asparagine, glutamine, cysteine, tyrosine, lysine, aspartic acid, and glutamic acid. Additionally, the adenylosuccinate synthetase variant may include an amino acid sequence where the 85th amino acid from the N-terminus in the amino acid sequence of SEQ ID NO: 2 is substituted with a different amino acid, which has the amino acid sequence of the adenylosuccinate synthetase variant or an amino acid sequence having 80% or more homology or identity to the amino acid sequence of the adenylosuccinate synthetase variant, but the amino acid sequence is not limited thereto. Specifically, the adenylosuccinate synthetase variant of the present disclosure may include a polypeptide having at least 80%, 85%, 90%, 95%, 96%, 97%, 98%, or 99% or more homology or identity to the amino acid sequence, where the 85th amino acid in the amino acid sequence of SEQ ID NO: 2 is substituted with an amino acid selected from the group consisting of serine, alanine, valine, leucine, methionine, isoleucine, threonine, asparagine, glutamine, cysteine, tyrosine, lysine, aspartic acid, and glutamic acid. Additionally, it is apparent that any amino acid sequence having the above sequence homology or identity and exhibiting an effect corresponding to that of the protein must also belong to the scope of the present disclosure, even if part of the amino acid sequence may have deletion, modification, substitution, or addition in part of the sequence, in addition to the amino acid at the 85th position.

That is, although the present disclosure describes "protein or polypeptide having the amino acid sequence of a particular SEQ ID NO", it is apparent that a protein having an amino acid sequence with deletion, modification, substitution, or addition in part of the sequence can also be used in the present disclosure, as long as the protein has activity identical or corresponding to that of the polypeptide comprised of an amino acid sequence of the corresponding SEQ ID NO. For example, as long as a protein has the activity identical or corresponding to that of the polypeptide variant, it does not exclude sequence addition, naturally occurring mutation, silent mutation, or conservative substitution thereof which does not alter the functions of the protein, before and after the amino acid sequence. It is apparent that a protein having such a sequence addition or mutation also falls within the scope of the present disclosure.

The "conservative substitution" means replacement of an amino acid with another amino acid having similar structural and/or chemical properties. Such an amino acid substitution may generally occur based on similarity in polarity of residues, charge, solubility, hydrophobicity, hydrophilicity, and/or amphipathic nature. For example, positively charged (basic) amino acids include arginine, lysine, and histidine; and negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

Accordingly, in the present disclosure, the "variant" may further include conservative substitution and/or modification of at least one amino acid in the "protein or polypeptide having an amino acid sequence of a particular SEQ ID NO". For example, certain variants may include variants in which at least one part, such as a N-terminal leader sequence or transmembrane domain, is removed. Other variants may include variants in which a part is removed from the N-terminus and/or C-terminus of a mature protein. The variant may also include other modifications, including deletion or addition of amino acids, which have minimal effects on the properties and a secondary structure of the polypeptide. For example, the polypeptide may be conjugated to a signal (or leader) sequence at the N-terminus of a protein that co-translationally or post-translationally directs transfer of a protein. The polypeptide may also be conjugated to another sequence or a linker to facilitate identification, purification, or synthesis of the polypeptide. The term "variant" may be used interchangeably with modification, modified protein, modified polypeptide, mutant, mutein, divergent, etc., and any term may be used without limitation, as long as it is used in a sense of being modified.

Homology and identity mean a degree of relatedness between two given amino acid sequences or nucleotide sequences and may be expressed as a percentage.

The terms "homology" and "identity" may often be used interchangeably with each other.

Sequence homology or identity of a conserved polynucleotide or polypeptide may be determined by a standard alignment algorithm and default gap penalties established by a program to be used may be used in combination. Substantially, homologous or identical sequences may hybridize under moderately or highly stringent conditions along their entire sequence or at least about 50%, about 60%, about 70%, about 80%, or about 90% of the entire length. With regard to the polynucleotides to be hybridized, polynucleotides including a degenerate codon instead of a codon may also be considered.

Whether any two polynucleotide or polypeptide sequences have homology, similarity, or identity may be determined by, for example, a known computer algorithm such as the "FASTA" program using default parameters as in Pearson et al. (1988) (*Proc. Natl. Acad. Sci. USA* 85]: 2444). Alternatively, they may be determined using the Needleman-Wunsch algorithm (Needleman and Wunsch, 1970, *J. Mol. Biol.* 48: 443 to 453) as performed in the Needleman program of the EMBOSS package (EMBOSS: The European Molecular Biology Open Software Suite, Rice et al., 2000, *Trends Genet.* 16: 276 to 277) (version 5.0.0 or later) (including GCG program package (Devereux, J., et al., *Nucleic Acids Research* 12: 387 (1984)), BLASTP, BLASTN, FASTA (Atschul, [S.] [F.] et al., *J Molec Biol* 215]: 403 (1990); Guide to Huge Computers, Martin J. Bishop, [ED.,] Academic Press, *San Diego,* 1994, and [CARILLO ETA/.](1988) *SIAM J Applied Math* 48: 1073). For example, homology, similarity, or identity may be determined using BLAST or ClustalW of the National Center for Biotechnology Information.

Homology, similarity, or identity of polynucleotides or polypeptides may be determined by comparing sequence information using a GAP computer program (e.g., Needleman et al. (1970), *J Mol Biol* 48: 443) as disclosed in Smith and Waterman, *Adv. Appl. Math* (1981) 2:482. Briefly, the GAP program defines similarity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14: 6745, as disclosed by Schwartz and Dayhoff, eds., Atlas Of Protein Sequence And Structure, National Biomedical Research Foundation, pp. 353 to 358 (1979); (2) a penalty of 3.0 for each gap and an additional 0.10 penalty for each symbol in each gap (or gap open penalty 10, gap extension penalty 0.5); and (3) no penalty for end gaps. Therefore, the term "homology" or "identity", as used herein, represents relevance between sequences.

Additionally, it is apparent that a polynucleotide which can be translated, due to codon degeneracy, into a polypeptide variant comprised of an amino acid sequence where the $85^{th}$ amino acid from the N-terminus of the amino acid sequence of SEQ ID NO: 2 is substituted with a different amino acid, or a polypeptide variant having homology or identity thereto may also be included. Additionally, by hybridization under stringent conditions with a probe that can be prepared from a known gene sequence (e.g., a sequence complementary to all or part of the nucleotide sequence), any polynucleotide sequence encoding an adenylosuccinate synthetase variant including an amino acid sequence, where the $85^{th}$ amino acid of the amino acid sequence of SEQ ID NO: 2 is substituted with an amino acid selected from the group consisting of serine, alanine, valine, leucine, methionine, isoleucine, threonine, asparagine, glutamine, cysteine, tyrosine, lysine, aspartic acid, and glutamic acid, may be included without limitation.

Another aspect of the present disclosure relates to a polynucleotide encoding the adenylosuccinate synthetase variant, or a vector including the polynucleotide.

As used herein, the term "polynucleotide" refers to a DNA or RNA strand having more than a certain length as a nucleotide polymer, which is a long chain of nucleotide monomers connected by covalent bonds, and more specifically, to a polynucleotide fragment encoding the polypeptide variant.

The polynucleotide encoding the polypeptide variant of the present disclosure may include any polynucleotide sequence without limitation, as long as it encodes the polypeptide variant having the activity of adenylosuccinate synthetase. In the present disclosure, the gene encoding the amino acid sequence of adenylosuccinate synthetase is purA gene, and specifically, the gene may be derived from *Corynebacterium stationis*, but is not limited thereto.

Specifically, due to codon degeneracy or by considering codons preferred by a microorganism in which the polypeptide is able to be expressed, various modifications may be made in the coding region of the polynucleotide within the scope that does not change the amino acid sequence of the polypeptide. Any polynucleotide sequence may be included without limitation as long as it encodes the adenylosuccinate synthetase variant, where the 85$^{th}$ amino acid in the amino acid sequence of SEQ ID NO: 2 is substituted with a different amino acid.

Additionally, by hybridization under stringent conditions with a probe that can be prepared from a known gene sequence (e.g., a sequence complementary to all or part of the nucleotide sequence), any sequence encoding a protein having the activity of an adenylosuccinate synthetase variant, where the 85$^{th}$ amino acid in the amino acid sequence of SEQ ID NO: 2 is substituted with a different amino acid, may be included without limitation.

The "stringent conditions" refer to conditions that enable specific hybridization between polynucleotides. Such conditions are described in detail in the literature (e.g., J. Sambrook et al., supra). The stringent conditions may include conditions under which genes having high homology or identity (e.g., genes having 40% or more, specifically 90% or more, more specifically 95% or more, still more specifically 97% or more, particularly specifically 99% or more homology or identity) can hybridize to each other; conditions under which genes having lower homology or identity cannot hybridize to each other; or conditions which are common washing conditions for Southern hybridization (e.g., a salt concentration and a temperature corresponding to 60° C., 1×SSC, 0.1% SDS; specifically 60° C., 0.1×SSC, 0.1% SDS; more specifically 68° C., 0.1×SSC, 0.1% SDS, once, specifically, twice or three times).

Hybridization requires that two nucleic acids have complementary sequences, although mismatches between bases may be possible depending on hybridization stringency. The term "complementary" is used to describe the relationship between nucleotide bases that can hybridize to each another. For example, with respect to DNA, adenosine is complementary to thymine and cytosine is complementary to guanine. Accordingly, the present disclosure may also include isolated nucleic acid fragments complementary to the entire sequence as well as to substantially similar nucleic acid sequences.

Specifically, a polynucleotide having homology or identity may be detected using hybridization conditions including a hybridization step at $T_m$ of 55° C. and by utilizing the above-described conditions. Additionally, the $T_m$ value may be 60° C., 63° C., or 65° C., but is not limited thereto, and may be appropriately controlled by those skilled in the art according to the purpose.

The appropriate stringency for hybridizing polynucleotides depends on the length of the polynucleotides and the degree of complementation, and variables are well known in the art (see Sambrook et al., supra, 9.50 to 9.51, 11.7 to 11.8).

In the present disclosure, the gene encoding the amino acid sequence of the adenylosuccinate synthetase variant is purA gene, and the polynucleotide encoding the gene is the same as explained above.

In the present disclosure, the polynucleotide encoding the adenylosuccinate synthetase variant is also the same as explained above.

As used herein, the term "vector" refers to a DNA construct containing the nucleotide sequence of the polynucleotide encoding the target polypeptide which is operably linked to an appropriate control sequence such that the target polypeptide is expressed in an appropriate host. The control sequence may include a promoter to initiate transcription, any operator sequence to control such transcription, a sequence encoding an appropriate ribosome-binding site on mRNA, and a sequence to control termination of transcription and translation. Upon transformation into an appropriate host, the vector may replicate or function independently of the host genome, or may integrate into the genome itself.

The vector used in the present disclosure may not be particularly limited as long as the vector is replicable in the host cell, and any vector known in the art may be used. Examples of the vector commonly used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used, and as a plasmid vector, those based on pBR, pUC, pBluescriptII, pGEM, pTZ, pCL, pET, etc. may be used. Specifically, pDZ, pACYC177, pACYC184, pCL, pECCG117, pUC19, pBR322, pMW118, pCC1BAC vector, etc. may be used.

In an embodiment, the polynucleotide encoding the target polypeptide may be inserted into the chromosome through a vector for chromosomal insertion. The insertion of the polynucleotide into the chromosome may be performed using any method known in the art (e.g., by homologous recombination), but the method is not limited thereto. A selection marker for confirming the insertion of the vector into the chromosome may be further included. The selection marker was used for selection of cells transformed with the vector (i.e., for confirmation of presence of the insertion of the target nucleic acid molecule), and markers capable of providing selectable phenotypes (e.g., drug resistance, auxotrophy, resistance to cytotoxic agents, and expression of surface polypeptides) may be used. Under the circumstances where selective agents are treated, only the cells capable of expressing the selection markers can survive or express other phenotypic traits, and thus the transformed cells can be easily selected.

Still another aspect of the present disclosure provides a microorganism producing purine nucleotides by containing the adenylosuccinate synthetase variant or a polynucleotide encoding the adenylosuccinate synthetase variant. Specifically, the microorganism containing the adenylosuccinate synthetase variant and/or the polynucleotide encoding the adenylosuccinate synthetase variant may be a microorganism prepared by transformation using a vector containing the polynucleotide, but the microorganism is not limited thereto.

As used herein, the term "transformation" refers to a process of introducing a vector which includes a polynucleotide encoding a target protein into a host cell such that the protein encoded by the polynucleotide can be expressed in the host cell. It does not matter whether the transformed polynucleotide is inserted into the chromosome of the host cell and located thereon or located outside of the chromosome, as long as the transformed polynucleotide can be expressed in the host cell. Further, the polynucleotide may include DNA and RNA encoding the target protein. The polynucleotide may be introduced in any form, as long as the polynucleotide can be introduced into the host cell and expressed therein. For example, the polynucleotide may be introduced into the host cell in the form of an expression cassette, which is a gene construct including all elements required for its autonomous expression. The expression cassette may include a promoter, a transcription termination signal, a ribosome binding site, and a translation termination signal that may be operably linked to the polynucleotide. The expression cassette may be in a form of an expression vector performing self-replication. In addition, the polynucleotide may be introduced into the host cell as is to be operably linked to the sequence required for expression in the host cell, but is not limited thereto.

Additionally, the term "operably linked" refers to a functional linkage between the gene sequence and a promoter sequence which initiates and mediates transcription of the polynucleotide encoding the target polypeptide of the present disclosure.

The term "microorganism including a polypeptide variant" or "microorganism including an adenylosuccinate synthetase variant", as used herein, refers to a microorganism provided with IMP productivity or XMP productivity in a microorganism, which naturally has a weak IMP productivity or its parent strain has no IMP productivity or XMP productivity. Specifically, the microorganism may be a microorganism expressing an adenylosuccinate synthetase variant including at least one amino acid variation in the amino acid sequence of SEQ ID NO: 2, and the amino acid modification may include the substitution of the 85$^{th}$ amino acid from the N-terminus of the amino acid sequence of SEQ ID NO: 2 with a different amino acid. Additionally, the microorganism may be a microorganism that expresses a polypeptide variant having the adenylosuccinate synthetase activity, where the 85$^{th}$ amino acid in the amino acid sequence of SEQ ID NO: 2 is substituted with a different amino acid, but the microorganism is not limited thereto.

The microorganism may be a cell or microorganism which contains a polynucleotide encoding an adenylosuccinate synthetase variant, or a cell or microorganism which is transformed with a vector and is able to express an adenylosuccinate synthetase variant. For the purpose of the present disclosure, the host cell or microorganism may be any microorganism that can express purine nucleotides by containing the adenylosuccinate synthetase variant.

In the present disclosure, the term "microorganism producing purine nucleotides" may be used interchangeably with "purine nucleotide-producing microorganism" and "microorganism having purine nucleotide productivity".

For the purpose of the present disclosure, the term "purine nucleotide" refers to a nucleotide including a purine-based structure, for example, IMP or XMP, but the purine nucleotide is not limited thereto.

In the present disclosure, the term "microorganism producing purine nucleotides" may be a microorganism where a genetic modification has occurred or activity has been enhanced for the desired purine nucleotide production, including both a wild-type microorganism or microorganisms where a natural or artificial genetic modification has occurred, and the microorganism may be a microorganism where a particular mechanism is enhanced or weakened due to reasons such as insertion of an exogenous gene, enhancement or inactivation of activity of an endogenous gene, etc. For the purpose of the present disclosure, the microorganism producing purine nucleotides is characterized in that it has increased productivity of the desired purine nucleotides by containing the adenylosuccinate synthetase variant, and specifically, the microorganism may be a microorganism of the genus *Corynebacterium*. Specifically, the microorganism producing purine nucleotides or microorganism having purine nucleotide productivity may be a microorganism where part of the gene involved in the purine nucleotide biosynthesis pathway is enhanced or weakened, or part of the gene involved in the purine nucleotide degradation pathway is enhanced or weakened. For example, the microorganism may be a microorganism where expression of purF encoding phosphoribosylpyrophosphate amidotransferase is enhanced or expression of guaB encoding inosine-5'-monophosphate dehydrogenase corresponding to IMP degradation pathway is weakened, but the microorganism is not limited thereto.

As used herein, the term "microorganism of the genus *Corynebacterium* producing 5'-purine nucleotides" refers to a microorganism of the genus *Corynebacterium* which has purine nucleotide productivity naturally or by modification. Specifically, as used herein, the microorganism of the genus *Corynebacterium* having purine nucleotide productivity may be a microorganism of the genus *Corynebacterium* which has improved purine nucleotide productivity by enhancing or weakening the activity of the purA gene encoding adenylosuccinate synthetase. More specifically, as used herein, the microorganism of the genus *Corynebacterium* having purine nucleotide productivity may be a microorganism of the genus *Corynebacterium* which has improved purine nucleotide productivity by including the adenylosuccinate synthetase variant of the present disclosure or the polynucleotide encoding the same, or by being transformed with a vector including the polynucleotide encoding the adenylosuccinate synthetase variant. The "microorganism of the genus *Corynebacterium* having improved purine nucleotide productivity" refers to a microorganism having improved purine nucleotide productivity, compared to its parent strain before transformation or a non-variant microorganism. The "non-variant microorganism" refers to a wild-type strain itself, a microorganism that does not include the protein variant producing purine nucleotides, or a microorganism that is not transformed with the vector containing the polynucleotide encoding the adenylosuccinate synthetase variant.

As used herein, the "microorganism of the genus *Corynebacterium*" may be specifically *Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis*, etc., but the microorganism is not limited thereto.

Still another aspect of the present disclosure provides a method of preparing purine nucleotides, which includes culturing the microorganism of the genus *Corynebacterium* that produces purine nucleotide in a medium, and recovering the purine nucleotides from the microorganism or the medium.

In the above method, culturing the microorganism may be performed by a known batch culture, continuous culture, fed-batch culture, etc., but the method of cultivation is not particularly limited thereto. In particular, the culture conditions may not be particularly limited, but an optimal pH (e.g., pH 5 to pH 9, specifically pH 6 to pH 8, and most specifically pH 6.8) may be adjusted using a basic compound (e.g., sodium hydroxide, potassium hydroxide, or ammonia) or an acidic compound (e.g., phosphoric acid or sulfuric acid), and an aerobic condition may be maintained by adding oxygen or oxygen-containing gas mixture to the culture. The culture temperature may be maintained at 20° C. to 45° C., and specifically at 25° C. to 40° C., and the cultivation may be performed for about 10 hours to about 160 hours, but the conditions are not limited thereto. 5'-Inosinic acid produced by the cultivation may be secreted into the medium or may remain within the cells.

Furthermore, in the culture medium to be used, as a carbon source, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but the carbon source is not limited thereto. As a nitrogen source, a nitrogen-containing organic compound (e.g., peptone, yeast extract, meat extract, malt extract, corn steep liquor, soybean flour, and urea) or an inorganic compound (e.g., ammonium sulfate, ammonium chloride, ammonium phosphate, ammonium carbonate, and ammonium nitrate), etc. may be used alone or in combination, but the nitrogen source is not limited thereto. As a phosphorus source, potassium dihydrogen phosphate, dipotassium hydrogen phosphate, a sodium-containing salt corresponding thereto, etc. may be used alone or in combination, but the phosphorus source is not limited thereto. Additionally, the medium may also include essential growth-promoting materials such as other metal salts (e.g., magnesium sulfate or iron sulfate), amino acids, and vitamins.

A method of recovering purine nucleotides produced in the cultivation step of the present disclosure is to collect the desired purine nucleotides from the culture using an appropriate method known in the art according to the cultivation method. For example, centrifugation, filtration, anion exchange chromatography, crystallization, HPLC, etc. may be used, and the desired purine nucleotides may be recovered from the medium or microorganism using an appropriate method known in the art.

Additionally, the recovering step may include a purification process. The purification process may be performed using an appropriate method known in the art. Therefore, the recovered purine nucleotides may be in a purified form or a microbial fermentation liquid including purine nucleotides (Introduction to Biotechnology and Genetic Engineering, A. J. Nair, 2008).

Advantageous Effects of the Invention

When a microorganism of the genus *Corynebacterium* producing purine nucleotides using the adenylosuccinate synthetase variant of the present disclosure, it is possible to produce purine nucleotides in high yield.

DETAILED DESCRIPTION OF THE INVENTION

Hereinafter, the present disclosure will be described in detail through exemplary embodiments. However, it will be apparent to those skilled in the art to which the present disclosure belongs that these exemplary embodiments are provided for the purpose of illustration only and are not intended to limit the scope of the present disclosure.

Example 1: Preparation of Wild-Type Based IMP-Producing Strain

The wild-type strain of the genus *Corynebacterium* cannot produce IMP at all or can produce only a very small amount even if it is possible. Accordingly, an IMP-producing strain was prepared based on *Corynebacterium stationis* ATCC6872. More specifically, the IMP-producing strain was prepared by enhancing the activity of purF gene encoding phosphoribosylpyrophosphate amidotransferase, which is the first enzyme of purine biosynthesis, and weakening the activity of guaB gene encoding 5'-inosinic acid dehydrogenase that corresponds to the IMP degradation pathway.

Example 1-1: Preparation of purF-Enhanced Strain

To prepare a strain in which the start codon of purF gene is modified, an insertion vector containing the purF gene of SEQ ID NO: 3 was prepared. To clone the purF gene into an insertion vector, specifically, PCR was performed using the genomic DNA of *Corynebacterium stationis* ATCC6872 as a template and primers of SEQ ID NOS: 4 and 5 and SEQ ID NOS: 6 and 7 for 30 cycles of denaturation at 94° C. for 30 sec, annealing at 55° C. for 30 sec, and extension at 72° C. for 2 min. PCR was performed again using two DNA fragments obtained by the above PCR as a template and primers of SEQ ID NOS: 4 and 72 for 30 cycles of denaturation at 94° C. for 30 sec, annealing at 55° C. for 30 sec, and extension at 72° C. for 2 min to obtain DNA fragments. The obtained DNA fragments were digested with a restriction enzyme XbaI, and cloned into the pDZ vector (Korean Patent No. 10-0924065 and International Publication No. 2008-033001) digested with the same enzyme. The thus-prepared vector was named as pDZ-purF-g1a.

TABLE 1

| SEQ ID NO | Primer | Sequence (5'-3') |
|---|---|---|
| 4 | purF g1a-1 | GCTCTAGACCACTCTAAGACGCGGCCACC |
| 5 | purF g1a-2 | AAGTAGTGTTCACCATGACGCTGATTCTACTAAGTTT |
| 6 | purF g1a-3 | AGTAGAATCAGCGTCATGGTGAACACTACTTTCCCCAG |
| 7 | purF g1a-4 | GCTCTAGACTGTGCGCCCACGATATCCAG |

The recombinant vector pDZ-purF-g1a was transformed into *Corynebacterium stationis* ATCC6872 by electroporation, and strains in which the vector was inserted into the genomic DNA by homologous recombination were selected on a medium containing 25 mg/L kanamycin. The selected primary strains were subjected to secondary crossover, and these selected strains were subjected to sequencing, and thereby the desired strain into which the mutation was introduced was selected. The strain was named as ATCC6872::purF(g1a) strain.

Example 1-2: Preparation of guaB-Weakened Strain

To prepare a strain in which the start codon of guaB gene is modified, an insertion vector containing the guaB gene of SEQ ID NO: 8 was prepared. To clone the guaB gene into the insertion vector, specifically, PCR was performed using the genomic DNA of *Corynebacterium stationis* ATCC6872 as a template and primers of SEQ ID NOS: 9 and 10 and SEQ ID NOS: 11 and 12. The PCR products were cloned as in Example 1-1, and the vector prepared was named as pDZ-guaB-a1t. The vector was introduced into the ATCC6872::purF(g1a) and the strain in which the above mutation was introduced was finally selected.

The finally selected wild-type *Corynebacterium stationis* ATCC6872-based strain producing IMP was named as CJI2330.

TABLE 2

| SEQ ID NO | Primer | Sequence (5'-3') |
|---|---|---|
| 9 | guaB alt-1 | GCTCTAGACTACGACAACACGGTGCCTAA |
| 10 | guaB alt-2 | CACGATTTTCGGTCAATACGGGTCTTCTCCTTCGCAC |
| 11 | guaB alt-3 | AGGAGAAGACCCGTATTGACCGAAAATCGTGTTTCT |
| 12 | guaB alt-4 | GCTCTAGAATCGACAAGCAAGCCTGCACG |

Example 1-3: Fermentation Titer Test of CJI2330

After dispensing a seed culture medium (2 mL) into test tubes (diameter: 18 mm), the tubes were autoclaved. Each of ATCC6872 and CJI2330 was inoculated and incubated at 30° C. for 24 h with shaking and used as a seed culture. A fermentation medium (29 mL) was dispensed into each 250 mL shaking Erlenmeyer flask, and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of IMP production was measured by HPLC (SHIMAZDU LC20A), and the culture results are as in Table 3 below. The following results suggest that the purf-enhanced and guaB-weakened strain has IMP productivity.

| Strain | IMP (g/L) |
|---|---|
| ATCC6872 | 0 |
| CJI2330 | 0.50 |

Seed culture medium: 1% glucose, 1% peptone, 1% meat extract, 1% yeast extract, 0.25% sodium chloride, 100 mg/L adenine, 100 mg/L guanine, pH 7.5

Fermentation medium: 0.1% sodium glutamate, 1% ammonium chloride, 1.2% magnesium sulfate, 0.01% calcium chloride, 20 mg/L iron sulfate, 20 mg/L manganese sulfate, 20 mg/L zinc sulfate, 5 mg/L copper sulfate, 23 mg/L L-cysteine, 24 mg/L alanine, 8 mg/L nicotinic acid, 45 μg/L biotin, 5 mg/L thiamine hydrochloride, 30 mg/L adenine, 1.9% phosphoric acid (85%), 2.55% glucose, 1.45% fructose

Example 2: Preparation of Adenylosuccinate Synthetase-Weakened Variant

To discover an adenylosuccinate synthetase variant capable improving purine nucleotide productivity, a mutant library of purA gene encoding adenylosuccinate synthetase was prepared.

Example 2-1: Preparation of Vector Containing purA Gene

To prepare a mutant library of purA gene, a recombinant vector containing the purA gene was first prepared. PCR was performed using the genomic DNA of *Corynebacterium stationis* ATCC6872 as a template and primers of SEQ ID NO: 13 and SEQ ID NO: 14, and the PCR product was cloned into *E. coli* vector pCR2.1 using a TOPO Cloning Kit (Invitrogen) to obtain pCR-purA.

TABLE 4

| SEQ ID NO | Primer | Sequence (5'-3') |
|---|---|---|
| 13 | purA 5' primer F (temp) | ATGGCTAAATACATTATCACT |
| 14 | purA 3' primer R (temp) | TGTGCTGGAGACCCCTCATAG |

Example 2-2: Preparation of Mutant Library of purA Gene

A mutant library of purA gene was prepared based on the vector prepared in Example 2-1. The library was prepared using an error-prone PCR kit (Clontech Diversify® PCR Random Mutagenesis Kit). Under conditions where mutations may occur, PCR was performed using primers of SEQ ID NO: 15 and SEQ ID NO: 16. Specifically, under conditions where 0 to 3 mutations per 1000 bp may occur, pre-heating was performed at 94° C. for 30 sec, followed by 25 cycles of 94° C. for 30 sec and 68° C. for 1 min 30 sec. A PCR product thus obtained was subjected to PCR using a megaprimer (500 ng to 125 ng) for 25 cycles of 95° C. for 50 sec, 60° C. for 50 sec, and 68° C. for 12 min, treated with DpnI, and transformed into *E. coli* DH5α and spread on an LB solid medium containing kanamycin (25 mg/L). After selecting 20 different kinds of transformed colonies, plasmids were obtained therefrom and subjected to sequencing analysis. As a result, it was confirmed that mutations were introduced at different sites at a frequency of 2 mutations/kb. About 20,000 transformed *E. coli* colonies were collected and the plasmids were extracted, and named as a pTOPO-purA-library.

TABLE 5

| SEQ ID NO | Primer | Sequence (5'-3') |
|---|---|---|
| 15 | purA error PCR primer F | AAGGGCAAAGCTACAGACATC |
| 16 | purA error PCR primer R | CCGCCGAGCATGAGAACCCGA |

Example 3: Evaluation of Prepared Library and Selection of Strain

Example 3-1: Evaluation of Library

The pTOPO-purA-library prepared in Example 2-2 was transformed into the CJI2330 strain prepared in Example 1 by electroporation, and the strain was spread on a nutrient medium containing 25 mg/L kanamycin to obtain 10,000 colonies into which the mutant gene was inserted. Each of the colonies was named as CJI2330::pTOPO_purA(mt)1 to CJI2330::pTOPO_purA(mt)10000.

Nutrient medium: 1% peptone, 1% meat extract, 0.25% sodium chloride, 1% yeast extract, 2% agar, pH 7.2

Each of the obtained 10,000 colonies was inoculated in 200 μL of an autoclaved seed culture medium, and cultured in a 96-deep well plate with shaking at 30° C., 1200 rpm for 24 hours using a microplate shaker (TAITEC), and used as a seed culture. The autoclaved fermentation medium (290

μL) was dispensed into a 96-deep well plate, and 20 μL of each of the seed cultures was inoculated thereto, followed by culturing with shaking under the same conditions as above for 72 hours.

To analyze the 5'-inosinic acid produced in the culture medium, after completion of the culture, 3 μL of the culture supernatant was transferred to a 96-well UV-plate, where each well contained 197 μL of distilled water, and shaken for 30 sec using a microplate reader, and absorbance was measured 270 nm at 25° C. using a spectrophotometer. The absorbance was compared with that of the CJI2330 strain, and 50 colonies of mutant strains showing a 10% or more increase in the absorbance were selected. Other colonies showed similar or decreased absorbance compared to the control.

The absorbance of the 50 selected strains was measured in the same manner as above to repeatedly examine the amount of 5'-inosinic acid production. One strain, CJI2330::pTOPO_purA(mt)333, which showed a significant improvement in 5'-inosinic acid productivity compared to the CJI2330 strain, was selected.

To confirm the validity of selected mutants, a fermentation titer test was performed.

After dispensing a seed culture medium (2 mL) into test tubes (diameter: 18 mm), the tubes were autoclaved. Each of CJI2330 and CJI2330::pTOPO_purA(mt)333 was inoculated and incubated at 30° C. for 24 h with shaking and used as a seed culture. A fermentation medium (29 mL) was dispensed into each 250 mL shaking Erlenmeyer flask, and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of IMP production was measured by HPLC (SHIMAZDU LC20A), and the culture results are as in Table 6 below.

TABLE 6

| Strain | IMP (g/L) |
|---|---|
| CJI2330 | 0.50 |
| CJI2330::pTOPO_purA(mt)333 | 0.61 |

As can be seen from the above results, it was confirmed that the amount of IMP was increased by about 122% in the strain where a vector containing a purA gene mutation compared to the CJI2330 strain. Accordingly, it was determined that the selected mutation in the library was valid.

Example 3-2: Confirmation of purA Variation

To confirm the gene variation of the mutant strain, PCR was performed in the CJI2330::pTOPO_purA(mt)333 strain using primers of SEQ ID NOS: 17 and 18, and the PCR product was subjected to sequencing, thereby confirming the presence of variation in the purA gene.

TABLE 7

| SEQ ID NO | Primer | Sequence (5'-3') |
|---|---|---|
| 17 | purA seq F | GACGCGTCGGAATCGCCGATA |
| 18 | purA seq R | CCGCCGAGCATGAGAACCCGA |

Specifically, it was confirmed that the purA gene of the CJI2330::pTOPO_purA(mt)333 strain includes a variation where the $85^{th}$ amino acid (i.e., glycine) of the purA amino acid sequence represented by SEQ ID NO: 2 is substituted with serine (i.e., the $253^{rd}$ nucleotide, 'g', is substituted with a nucleotide 'a'). Accordingly, in Examples hereinbelow, attempts were made to confirm whether the above variation can affect the amount of purine nucleotide production in each microorganism of the genus Corynebacterium.

Example 4: Confirmation of IMP Production in IMP-Producing Strain Derived from ATCC6872

An IMP-producing strain derived from ATCC6872 was prepared, and the variation confirmed in Example 3 was introduced into the strain and the IMP productivity of the strain was confirmed.

Example 4-1: Selection of IMP-Producing Strain Derived From ATCC6872

To prepare an IMP-producing strain derived from the ATCC6872 strain, the culture of ATCC6872 was suspended in a phosphate buffer (pH 7.0) or citrate buffer (pH 5.5) at a density of $10^7$ cells/mL to $10^8$ cells/mL and treated with UV at room temperature or 32° C. for 20 min to 40 min to induce a mutation. The strain was washed with a 0.85% saline solution twice and spread, after dilution, on a minimal medium containing 1.7% agar which was supplemented with a resistance-providing material at an appropriate concentration, and thereby colonies were obtained. Each colony was cultured in a nutrient medium and then cultured in a seed culture medium for 24 hours. After culturing each colony in a fermentation medium for 3 to 4 days, colonies which showed excellent production of IMP accumulated in the culture medium were selected. To prepare a strain producing IMP at high concentration, adenine-auxotroph, guanine-leaky type, lysozyme sensitivity, 3,4-dehydroproline resistance, streptomycin resistance, sulfaguanidine resistance, norvaline resistance, and trimethoprim resistance were provided by performing the corresponding procedures in a sequential manner. As a result, the CJI12335 strain provided with resistance to the above materials and having excellent IMP productivity was finally selected. The resistances of the CJI2332 strain relative to those of ATCC6872 were compared and the results are shown in the following Table 8.

TABLE 8

| Characteristic | ATCC6872 | CJI2332 |
|---|---|---|
| Adenine-auxotroph | Non-auxotroph | Auxotroph |
| Guanine-leaky type | Non-auxotroph | Leaky type |
| Lysozyme sensitivity | 80 μg/mL | 8 μg/mL |
| 3,4-Dehydroproline resistance | 1000 μg/mL | 3,500 μg/mL |
| Streptomycin resistance | 500 μg/mL | 2,000 μg/mL |
| Sulfaguanidine resistance | 50 μg/mL | 200 μg/mL |
| Norvaline resistance | 0.2 mg/mL | 2 mg/mL |
| Trimethoprim resistance | 20 μg/mL | 100 μg/mL |

Minimal medium: 2% glucose, 0.3% sodium sulfate, 0.1% monopotassium phosphate, 0.3% dipotassium phosphate, 0.3% magnesium sulfate, 10 mg/L calcium chloride, 10 mg/L iron sulfate, 1 mg/L zinc sulfate, 3.6 mg/L manganese chloride, 20 mg/L L-cysteine, 10 mg/L calcium pantothenate, 5 mg/L thiamine hydrochloride, 30 μg/L biotin, 20 mg/L adenine, 20 mg/L guanine, adjusted to pH 7.3.

Example 4-2: Fermentation Titer Test of CJI2332

After dispensing a seed culture medium (2 mL) into test tubes (diameter: 18 mm), the tubes were autoclaved. Each of ATCC6872 and CJI2332 was inoculated and incubated at 30° C. for 24 hours with shaking and used as a seed culture. A fermentation medium (29 mL) was dispensed into each 250 mL shaking Erlenmeyer flask, and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of IMP production was measured by HPLC (SHIMAZDU LC20A), and the culture results are as in Table 9 below.

TABLE 9

| Strain | IMP (g/L) |
|---|---|
| ATCC6872 | 0 |
| CJI2332 | 1.74 |

Example 4-3: Preparation of Insertion Vector Containing purA Variation

To introduce the variations selected in Example 3 into the strains, an insertion vector was prepared. The process for preparing the vector for introduction of purA(G85S) variation is as follows. PCR was performed using the CJI2330::Topo_purA(G85S) as a template and primers of SEQ ID NO: 55 and SEQ ID NO: 56. PCR was performed as follows: denaturation at 94° C. for 5 min; 20 cycles of denaturation at 94° C. for 30 sec, annealing at 55° C. for 30 sec, and polymerization at 72° C. for 1 min; and polymerization at 72° C. for 5 min. The thus obtained gene fragments were each digested with XbaI. Each gene fragment was cloned into a linear pDZ vector digested with XbaI using T4 ligase, and thereby the pDZ-purA(G85S) vector was prepared.

TABLE 10

| SEQ ID NO | Primer | Sequence (5'-3') |
|---|---|---|
| 55 | purA(G85S) F' | GCTCTAGATGCCGGCATTTTTCGAAGC |
| 56 | purA(G85S) R | GCTCTAGAAAGTAGTCGGTAAAGCCGTTG |

Example 4-4: Introduction of Variants into CJI2330 and CJI2332 Strains Derived from ATCC6872 and their Evaluation The purA variation was introduced to each of the wild-type-derived IMP-producing CJI2330 strain prepared in Example 1 and the CJI2332 strain selected in Example 4-1, and the amount of IMP produced by each strain was evaluated. To confirm the presence of a variation in the purA gene, the chromosomal DNA of the CJI2332 strain was amplified by PCR. Specifically, first, purA gene fragments were amplified by PCR using the chromosomal DNA of the CJI2332 strain as a template and primers of SEQ ID NOS: 17 and 18, in which the PCR was performed by 28 cycles of denaturation at 94° C. for 1 min; annealing at 58° C. for 30 sec, and polymerization at 72° C. for 2 min using Taq DNA polymerase. The nucleotide sequences of the amplified purA fragments were analyzed using the same primers, and as a result, it was confirmed that there was no variation in the purA gene of the CJI2332 strain.

Then, the pDZ-purA(G85S) vector was transformed into the CJI2330 strain and the CJI2332 strain, and the strains in which the vector was inserted on the genomic DNA by recombination of homologous sequences were selected on a medium containing kanamycin (25 mg/L). The selected primary strains were subjected to secondary crossover, and thereby the strains in which a variation of the target gene was introduced were selected. For confirmation of the introduction of the gene variation in the desired transformed strains, PCR was performed using primers of SEQ ID NO: 17 and SEQ ID NO: 18 and the PCR products were confirmed by sequence analysis. As a result, it was confirmed that the gene variation was introduced into the strains. The thus-prepared strains were named as CJI2330::purA(G85S) and CJI2332::purA(G85S), respectively.

The IMP productivity for each of CJI2330, CJI2332, CJI2330::purA(G85S), and CJI2332::purA(G85S) strains was evaluated. After the completion of culture, the amount of IMP production by each strain was measured by a method using HPLC, and the culture results are shown in Table 11 below.

TABLE 11

| Strain | IMP (g/L) |
|---|---|
| CJI2330 | 0.50 |
| CJI2330::purA(G85S) | 0.61 |
| CJI2332 | 1.74 |
| CJI2332::purA(G85S) | 2.03 |

In the above results, it was confirmed that the strain in which the purA gene variation was introduced showed an increase in the amount of IMP production by about 122% and about 116% compared to the wild-type-derived IMP-producing CJI2330 and CJI2332 strains, respectively.

The CJI2332 strain was deposited at the Korean Culture Center of Microorganisms (KCCM) on Jun. 22, 2018, under the provisions of the Budapest Treaty and assigned accession number KCCM12277P. Additionally, the prepared CJI2332::purA(G85S) strain, also called CJI2348, was deposited at the KCCM on Jun. 22, 2018, under the provisions of the Budapest Treaty and assigned accession number KCCM12280P.

Example 5: Confirmation of 5'-Xanthylic Acid Productivity by purA Gene Variation

Example 5-1: Selection of XMP-Producing Strains Derived from ATCC6872

To prepare a 5'-xanthosine monophosphate (XMP)-producing strain derived from ATCC6872, the *Corynebacterium stationis* ATCC6872 strain was suspended in the phosphate buffer (pH 7.0) or citrate buffer (pH 5.5) at a density of $10^7$ cells/mL to $10^8$ cells/mL and treated with UV at room temperature or 32° C. for 20 min to 40 min to induce a mutation. The strain was washed with a 0.85% saline solution twice and spread, after dilution, on a minimal medium containing 1.7% agar which was supplemented with a resistance-providing material at an appropriate concentration, and thereby colonies were obtained. Each colony was cultured in a nutrient medium and then cultured in a seed culture medium for 24 h. After culturing each colony in a fermentation medium for 3 to 4 days, colonies which showed excellent production of XMP accumulated in the culture medium were selected. Specifically, strains were selected from those which can grow in a medium where fluorotryptophan is added according to concentrations (addition medium), and more specifically, from those which can grow in a medium with a fluorotryptophan concentration of 100 mg/L and has an improved concentration of 5'-xanthylic acid. The selected strain was named as CJX1664.

Minimal medium: glucose 20 g/L, monopotassium phosphate 1 g/L, dipotassium phosphate 1 g/L, urea 2 g/L, ammonium sulfate 3 g/L, magnesium sulfate 1 g/L, calcium chloride 100 mg/L, iron sulfate 20 mg/L, manganese sulfate 10 mg/L, zinc sulfate 10 mg/L, biotin 30 μg/L, thiamine hydrochloride 0.1 mg/L, copper sulfate 0.8 mg/L, adenine 20 mg/L, guanine 20 mg/L, pH 7.2

Addition medium: a medium where fluorotryptophan at a concentration of 10 mg/L, 20 mg/L, 50 mg/L, 70 mg/L, 100 mg/L, and 200 mg/L is added to a minimal medium The biochemical characteristics of the CJX1664 strain are shown in Table 12 below. Referring to Table 12, the CJX1664 strain can be grown in an addition medium where a fluorotryptophan is added at a concentration of 100 mg/L.

TABLE 12

| Characteristics | ATCC6872 | CJX1664 |
| --- | --- | --- |
| Fluorotryptophan Resistance | 10 mg/L | 100 mg/L |

Example 5-2: CJX1664 Fermentation Titer Test

After dispensing a seed culture medium (2 mL) into test tubes (diameter: 18 mm), the tubes were autoclaved. Each of ATCC6872 and CJX1664 was inoculated and incubated at 30° C. for 24 h with shaking and used as a seed culture. A fermentation medium (29 mL) was dispensed into each 250 mL shaking Erlenmeyer flask, and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of XMP production was measured by HPLC (SHIMAZDU LC20A), and the culture results are as in Table 13 below.

TABLE 13

| Strain | XMP (g/L) |
| --- | --- |
| ATCC6872 | 0 |
| CJX1664 | 4.72 |

Example 5-3: Introduction of Variant into CJX1664 Strain and their Evaluation To confirm the presence of a variation of the purA gene of the CJX1664 strain selected in Example 5-1, the chromosomal DNA PCR of the CJX1664 strain was amplified by PCR. Specifically, first, purA fragments were amplified by PCR using the chromosomal DNA of the CJX1664 strain as a template and primers of SEQ ID NOS: 17 and 18, in which the PCR was performed by 28 cycles of denaturation at 94° C. for 1 min; annealing at 58° C. for 30 sec, and polymerization at 72° C. for 2 min using Taq DNA polymerase. The nucleotide sequences of the amplified purA gene fragments were analyzed using the same primers, and as a result, it was confirmed that there was no variation in the purA gene of the CJX1664 strain.

The vector prepared in Example 4-3 was transformed into the CJX1664 strain, and the strains in which the vector was inserted on the genomic DNA by recombination of homologous sequences were selected on a medium containing 25 mg/L kanamycin. The selected primary strains were subjected to secondary crossover, and thereby those strains in which a variation of the target gene was introduced were selected. The introduction of the gene variation in the desired transformed strains was confirmed by sequence analysis.

The XMP productivity for each of CJX1664 and CJX1664::purA(G85S) strains was evaluated. After the completion of culture, the amount of XMP production by each strain was measured by a method using HPLC, and the culture results are shown in Table 14 below.

TABLE 14

| Strain | XMP (g/L) |
| --- | --- |
| CJX1664 | 4.72 |
| CJX1664::purA(G85S) | 5.19 |

As can be seen in Table 14 above, the CJX1664::purA (G85S) strain showed an increase in the amount of XMP production by about 109% compared to the CJX1664 strain (i.e., an ATCC6872-based XMP-producing strain).

The CJX1664 strain was deposited at the Korean Culture Center of Microorganisms (KCCM) on Jul. 6, 2018, under the provisions of the Budapest Treaty and assigned accession number KCCM12285P. Additionally, the prepared CJX1664::purA(G85S) strain, also called CJX1665, was deposited at the KCCM on Jul. 6, 2018, under the provisions of the Budapest Treaty and assigned accession number KCCM12286P.

Example 6: Substitution of Amino Acid in purA Variation with Different Amino Acid

Example 6-1: Preparation of Vector for Insertion of Amino Acid in purA Variation Through the above Examples, it was confirmed that the purA(G85S) variation can improved the productivity of purine nucleotides. In this regard, to confirm the positional importance of the purA variation, the effect of the substitution of the $85^{th}$ amino acid with a different amino acid on the productivity of purine nucleotides was examined. The process of preparing the vector for the insertion of purA(G85S) variation is as follows. Site-directed mutagenesis was performed using the pDZ-purA(G85S) vector prepared in Example 4 as a backbone. Specifically, PCR was performed using the sequences shown in Table 15 as primers under the following conditions: 18 cycles of denaturation at 94° C. for 30 sec, annealing at 55° C. for 30 sec, and extension at 68° C. for 12 min. The resulting PCR products were digested with DpnI, transformed into a DH5α strain, and colonies were obtained therefrom. The plasmids of thus obtained colonies were obtained by a known plasmid extraction method, and the information of the obtained plasmids are shown below in Table 15.

TABLE 15

| SEQ ID NO | Primer | | Sequence (5'-3') |
|---|---|---|---|
| 21 | purA(G85A) | F | CTTTGAGGAAATTGAAGCTCTCGAAGCCCGCGGCGC |
| 22 | purA(G85A) | R | GCGCCGCGGGCTTCGAGAGCTTCAATTTCCTCAAAG |
| 23 | purA(G85V) | F | CTTTGAGGAAATTGAAGTCCTCGAAGCCCGCGGCGC |
| 24 | purA(G85V) | R | GCGCCGCGGGCTTCGAGGACTTCAATTTCCTCAAAG |
| 25 | purA(G85L) | F | CTTTGAGGAAATTGAACTGCTCGAAGCCCGCGGCGC |
| 26 | purA(G85L) | R | GCGCCGCGGGCTTCGAGCAGTTCAATTTCCTCAAAG |
| 27 | purA(G85M) | F | CTTTGAGGAAATTGAAATGCTCGAAGCCCGCGGCGC |
| 28 | purA(G85M) | R | GCGCCGCGGGCTTCGAGCATTTCAATTTCCTCAAAG |
| 29 | purA(G85I) | F | CTTTGAGGAAATTGAAATCCTCGAAGCCCGCGGCGC |
| 30 | purA(G85I) | R | GCGCCGCGGGCTTCGAGGATTTCAATTTCCTCAAAG |
| 31 | purA(G85T) | F | CTTTGAGGAAATTGAAACTCTCGAAGCCCGCGGCGC |
| 32 | purA(G85T) | R | GCGCCGCGGGCTTCGAGAGTTTCAATTTCCTCAAAG |
| 33 | purA(G85N) | F | CTTTGAGGAAATTGAAAACCTCGAAGCCCGCGGCGC |
| 34 | purA(G85N) | R | GCGCCGCGGGCTTCGAGGTTTTCAATTTCCTCAAAG |
| 35 | purA(G85Q) | F | CTTTGAGGAAATTGAACAGCTCGAAGCCCGCGGCGC |
| 36 | purA(G85Q) | R | GCGCCGCGGGCTTCGAGCTGTTCAATTTCCTCAAAG |
| 37 | purA(G85C) | F | CTTTGAGGAAATTGAATGCCTCGAAGCCCGCGGCGC |
| 38 | purA(G85C) | R | GCGCCGCGGGCTTCGAGGCATTCAATTTCCTCAAAG |
| 39 | purA(G85P) | F | CTTTGAGGAAATTGAACCACTCGAAGCCCGCGGCGC |
| 40 | purA(G85P) | R | GCGCCGCGGGCTTCGAGTGGTTCAATTTCCTCAAAG |
| 41 | purA(G85Y) | F | CTTTGAGGAAATTGAATACCTCGAAGCCCGCGGCGC |
| 42 | purA(G85Y) | R | GCGCCGCGGGCTTCGAGGTATTCAATTTCCTCAAAG |
| 43 | purA(G85W) | F | CTTTGAGGAAATTGAATGGCTCGAAGCCCGCGGCGC |
| 44 | purA(G85W) | R | GCGCCGCGGGCTTCGAGCCATTCAATTTCCTCAAAG |
| 45 | purA(G85K) | F | CTTTGAGGAAATTGAAAAGCTCGAAGCCCGCGGCGC |
| 46 | purA(G85K) | R | GCGCCGCGGGCTTCGAGCTTTTCAATTTCCTCAAAG |
| 47 | purA(G85R) | F | CTTTGAGGAAATTGAACGCCTCGAAGCCCGCGGCGC |
| 48 | purA(G85R) | R | GCGCCGCGGGCTTCGAGGCGTTCAATTTCCTCAAAG |
| 49 | purA(G85H) | F | CTTTGAGGAAATTGAACACCTCGAAGCCCGCGGCGC |
| 50 | purA(G85H) | R | GCGCCGCGGGCTTCGAGGTGTTCAATTTCCTCAAAG |
| 51 | purA(G85D) | F | CTTTGAGGAAATTGAAGATCTCGAAGCCCGCGGCGC |
| 52 | purA(G85D) | R | GCGCCGCGGGCTTCGAGATCTTCAATTTCCTCAAAG |
| 53 | purA(G85E) | F | CTTTGAGGAAATTGAAGAACTCGAAGCCCGCGGCGC |
| 54 | purA(G85E) | R | GCGCCGCGGGCTTCGAGTTCTTCAATTTCCTCAAAG |

TABLE 16

| No. | Plasmid |
|---|---|
| 1 | pDZ-purA G85A |
| 2 | pDZ-purA G85V |
| 3 | pDZ-purA G85L |
| 4 | pDZ-purA G85M |
| 5 | pDZ-purA G85I |
| 6 | pDZ-purA G85T |

TABLE 16-continued

| No. | Plasmid |
|---|---|
| 7 | pDZ-purA G85N |
| 8 | pDZ-purA G85 Q |
| 9 | pDZ-purA G85C |
| 10 | pDZ-purA G85P |
| 11 | pDZ-purA G85Y |
| 12 | pDZ-purA G85W |
| 13 | pDZ-purA G85K |
| 14 | pDZ-purA G85R |
| 15 | pDZ-purA G85H |
| 16 | pDZ-purA G85D |
| 17 | pDZ-purA G85E |

Example 6-2: Preparation of Strain where an Amino Acid is Substituted with a Different Amino Acid According to Position of Variation of a purA Variant, and Comparison of 5'-Inosinic Acid Productivities Each of the 18 kinds of vectors, for the introduction of variants, prepared in Example 6-1 was transformed into the CJI2332 strain, and those strains where these vectors were inserted into the genomic DNA by homologous recombination were selected on a medium containing 25 mg/L kanamycin. The selected primary strains were subjected to secondary crossover, and thereby those strains into which a variation of the target gene was introduced were selected. For confirmation of the introduction of the gene variation in the desired transformed strains, PCR was performed using primers of SEQ ID NO: 17 and SEQ ID NO: 18 and the PCR products were confirmed by sequence analysis. The strains were named according to the inserted varions as shown in Table 17.

TABLE 17

| No. | Strain |
|---|---|
| 1 | CJI2332::purA(G85A) |
| 2 | CJI2332::purA(G85V) |
| 3 | CJI2332::purA(G85L) |
| 4 | CJI2332::purA(G85M) |
| 5 | CJI2332::purA(G85I) |
| 6 | CJI2332::purA(G85T) |
| 7 | CJI2332::purA(G85N) |
| 8 | CJI2332::purA(G85Q) |
| 9 | CJI2332::purA(G85C) |
| 10 | CJI2332::purA(G85P) |
| 11 | CJI2332::purA(G85Y) |
| 12 | CJI2332::purA(G85W) |
| 13 | CJI2332::purA(G85K) |
| 14 | CJI2332::purA(G85R) |
| 15 | CJI2332::purA(G85H) |
| 16 | CJI2332::purA(G85D) |
| 17 | CJI2332::purA(G85E) |

The concentration of 5'-inosinic acid was analyzed by culturing the strains in the same manner as in Example 1.

TABLE 18

Concentration of 5'-inosinic acid with variation in purA (g/L)

| No. | Strain | Average 5'-Inosinic acid |
|---|---|---|
| | CJI2332 | 1.74 |
| Control Group | CJI2332::purA(G85S) | 2.03 |
| 1 | CJI2332::purA(G85A) | 1.93 |
| 2 | CJI2332::purA(G85V) | 1.84 |
| 3 | CJI2332::purA(G85L) | 2.01 |
| 4 | CJI2332::purA(G85M) | 2.01 |
| 5 | CJI2332::purA(G85I) | 2.02 |
| 6 | CJI2332::purA(G85T) | 2.02 |
| 7 | CJI2332::purA(G85N) | 1.83 |
| 8 | CJI2332::purA(G85Q) | 2.03 |
| 9 | CJI2332::purA(G85C) | 1.82 |
| 10 | CJI2332::purA(G85P) | 1.10 |
| 11 | CJI2332::purA(G85Y) | 1.92 |
| 12 | CJI2332::purA(G85W) | 0.39 |
| 13 | CJI2332::purA(G85K) | 1.86 |
| 14 | CJI2332::purA(G85R) | 1.30 |
| 15 | CJI2332::purA(G85H) | 1.67 |
| 16 | CJI2332::purA(G85D) | 2.02 |
| 17 | CJI2332::purA(G85E) | 1.94 |

Referring to Table 18 above, it was confirmed that the strains containing the purA, in which the $85^{th}$ amino acid of the amino acid sequence encoding the purA gene is substituted with a different amino acid, showed a significant change in the amount of IMP production, compared to other strains which did not contain the above variation. That is, it was confirmed that the $85^{th}$ amino acid of the amino acid sequence encoding the purA gene is an important position for variation associated with the production of purine nucleotides, and when the $85^{th}$ amino acid of the amino acid sequence encoding the purA gene is substituted with an amino acid selected from the group consisting of serine, alanine, valine, leucine, methionine, isoleucine, threonine, asparagine, glutamine, cysteine, tyrosine, lysine, aspartic acid, and glutamic acid, the microorganism having the variation can significantly increase the production of purine nucleotides.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polynucleotide encoding an adenylosuccinate synthetase variant having at least 90% sequence identity to the amino acid sequence of SEQ ID NO:2 and having adenylosuccinate synthetase activity, wherein the amino acid corresponding to position 85 of the amino acid sequence of SEQ ID NO: 2 is substituted with a different amino acid, wherein the different amino acid is selected from the group consisting of serine, alanine, valine, leucine, methionine, isoleucine, threonine, asparagine, glutamine, cysteine, tyrosine, lysine, aspartic acid, and glutamic acid, and wherein said adenylosuccinate synthetase variant has increased purine production relative to a wild type adenylosuccinate synthetase.

2. A vector comprising the polynucleotide of claim 1.

3. A microorganism of the genus *Corynebacterium* capable of producing purine nucleotides, comprising an adenylosuccinate synthetase variant having at least 90% sequence identity to the amino acid sequence of SEQ ID NO:2 and having adenylosuccinate synthetase activity, wherein the amino acid corresponding to position 85 of the amino acid sequence of SEQ ID NO: 2 is substituted with a different amino acid, wherein the different amino acid is selected from the group consisting of serine, alanine, valine, leucine, methionine, isoleucine, threonine, asparagine, glutamine, cysteine, tyrosine, lysine, aspartic acid, and glutamic acid, and wherein said adenylosuccinate synthetase variant has increased purine production relative to a wild type adenylosuccinate synthetase.

4. The microorganism according to claim 3, wherein the microorganism of the genus *Corynebacterium* is *Corynebacterium stationis*.

5. A method for preparing IMP, XMP or GMP, comprising:
culturing the microorganism of the genus *Corynebacterium* of claim 3 in a medium; and
recovering the IMP, XMP or GMP from the microorganism or the medium.

6. The method according to claim 5, wherein the microorganism of the genus *Corynebacterium* is *Corynebacterium stationis*.

7. A microorganism of the genus *Corynebacterium* capable of producing purine nucleotides, comprising the vector of claim 2.

8. The microorganism according to claim 7, wherein the microorganism of the genus *Corynebacterium* is *Corynebacterium stationis*.

9. A method for preparing IMP, XMP or GMP, comprising:
culturing the microorganism of the genus *Corynebacterium* of claim 7 in a medium; and
recovering the IMP, XMP or GMP from the microorganism or the medium.

10. The method according to claim 9, wherein the microorganism of the genus *Corynebacterium* is *Corynebacterium stationis*.

\* \* \* \* \*

SEQUENCE LISTING

<160> NUMBER OF SEQ ID NOS: 56

<210> SEQ ID NO 1
<211> LENGTH: 1293
<212> TYPE: DNA
<213> ORGANISM: Unknown
<220> FEATURE:

<223> OTHER INFORMATION: purA NT

<400> SEQUENCE: 1

| | | | | | |
|---|---|---|---|---|---|
| atggcagcta | tcgttatcgt | cggcgcccaa | tggggcgacg | aaggcaaggg | caaagctaca | 60 |
| gacatcctgg | gtggacgcgt | ggactacgtc | gtcaagccca | acggtggtaa | caatgctggc | 120 |
| cacaccgttg | tagtcggtgg | cgaaaagtac | gaactcaagc | tgctgcccgc | cggcatcctc | 180 |
| tccgaaaacg | ccgtgccagt | gctgggcaac | ggcgtagtta | tcaacctcga | agcactcttt | 240 |
| gaggaaattg | aaggcctcga | agcccgcggc | gctgatgctt | cccgcttgcg | tatttccgcc | 300 |
| aacgcgcacc | tggttgcgcc | ataccaccag | accttagacc | gcgtgcagga | acgtttcttg | 360 |
| ggcaagcgcg | cgattggcac | caccggccgc | ggtatcggcc | cagcttatgc | cgacaaggtc | 420 |
| gcgcgcgtgg | gagttcgcgt | gcaagacatc | ttcgacgaat | ccatcctgcg | tcagaaggtc | 480 |
| gaatccgcgc | tggatatcaa | aaaccagatg | ctggtcaaaa | tgtacaaccg | caaggcgatt | 540 |
| gaccctgaga | ccatcgtcga | atacttcctg | tcctaccgcg | accgcctcga | gcctatggtc | 600 |
| gtggactccg | agtacgagct | caacaccgct | ctggatgccg | gcaagcacgt | gctcatggaa | 660 |
| ggcggccagg | ccaccatgct | cgacgtggac | cacggcacct | acccattcgt | gacctcgtcc | 720 |
| aacccaaccg | ccggtggtgc | atcggtaggc | tctggcgtcg | ggcctacccg | catcacgcac | 780 |
| tccctgggca | tcattaaggc | gtacaccacc | cgcgttggtg | ctggcccatt | cccaaccgag | 840 |
| ctctttgaca | gtggggcga | ataccctccag | accaccggcg | cgaggtcgg | cgtcaacacc | 900 |
| ggccgcaccc | gtcgttgtgg | ctggtatgac | tctgtcattg | cacgctacgc | atcgcgcgtc | 960 |
| aacggcttta | ccgactactt | ccttactaaa | ctcgacgtgc | tcaccggcat | cggcgaaatc | 1020 |
| cctatttgcg | tcgcctacga | cgtcgatggc | gaacgcttcg | atgaaatgcc | gctgactcag | 1080 |
| tcgcagtttc | accacgcaca | accaatttat | gaaaccatgc | cagcgtggga | agaagacatc | 1140 |
| accggttgca | ccacctttga | ggagctgccg | caaaaggcac | aggattacgt | gctgcggcta | 1200 |
| gaggagctgt | ccggcacccg | catgtcatac | atcggcgttg | ccctggccg | tgaccagacc | 1260 |
| atcgtgcgcc | acgacgtgct | cgacgagaaa | taa | | | 1293 |

```
<210> SEQ ID NO 2
<211> LENGTH: 430
<212> TYPE: PRT
<213> ORGANISM: Unknown
<220> FEATURE:
<223> OTHER INFORMATION: purA AA
```

<400> SEQUENCE: 2

```
Met Ala Ala Ile Val Ile Val Gly Ala Gln Trp Gly Asp Glu Gly Lys
1               5                   10                  15

Gly Lys Ala Thr Asp Ile Leu Gly Gly Arg Val Asp Tyr Val Val Lys
            20                  25                  30

Pro Asn Gly Gly Asn Asn Ala Gly His Thr Val Val Gly Gly Glu
        35                  40                  45

Lys Tyr Glu Leu Lys Leu Leu Pro Ala Gly Ile Leu Ser Glu Asn Ala
    50                  55                  60

Val Pro Val Leu Gly Asn Gly Val Val Ile Asn Leu Glu Ala Leu Phe
65                  70                  75                  80

Glu Glu Ile Glu Gly Leu Glu Ala Arg Gly Ala Asp Ala Ser Arg Leu
                85                  90                  95

Arg Ile Ser Ala Asn Ala His Leu Val Ala Pro Tyr His Gln Thr Leu
            100                 105                 110
```

Asp Arg Val Gln Glu Arg Phe Leu Gly Lys Arg Ala Ile Gly Thr Thr
            115                 120                 125

Gly Arg Gly Ile Gly Pro Ala Tyr Ala Asp Lys Val Ala Arg Val Gly
        130                 135                 140

Val Arg Val Gln Asp Ile Phe Asp Glu Ser Ile Leu Arg Gln Lys Val
145                 150                 155                 160

Glu Ser Ala Leu Asp Ile Lys Asn Gln Met Leu Val Lys Met Tyr Asn
                165                 170                 175

Arg Lys Ala Ile Asp Pro Glu Thr Ile Val Glu Tyr Phe Leu Ser Tyr
            180                 185                 190

Arg Asp Arg Leu Glu Pro Met Val Val Asp Ser Glu Tyr Glu Leu Asn
        195                 200                 205

Thr Ala Leu Asp Ala Gly Lys His Val Leu Met Glu Gly Gly Gln Ala
210                 215                 220

Thr Met Leu Asp Val Asp His Gly Thr Tyr Pro Phe Val Thr Ser Ser
225                 230                 235                 240

Asn Pro Thr Ala Gly Gly Ala Ser Val Gly Ser Gly Val Gly Pro Thr
                245                 250                 255

Arg Ile Thr His Ser Leu Gly Ile Ile Lys Ala Tyr Thr Thr Arg Val
            260                 265                 270

Gly Ala Gly Pro Phe Pro Thr Glu Leu Phe Asp Lys Trp Gly Glu Tyr
        275                 280                 285

Leu Gln Thr Thr Gly Gly Glu Val Gly Val Asn Thr Gly Arg Thr Arg
    290                 295                 300

Arg Cys Gly Trp Tyr Asp Ser Val Ile Ala Arg Tyr Ala Ser Arg Val
305                 310                 315                 320

Asn Gly Phe Thr Asp Tyr Phe Leu Thr Lys Leu Asp Val Leu Thr Gly
                325                 330                 335

Ile Gly Glu Ile Pro Ile Cys Val Ala Tyr Asp Val Asp Gly Glu Arg
            340                 345                 350

Phe Asp Glu Met Pro Leu Thr Gln Ser Gln Phe His His Ala Gln Pro
        355                 360                 365

Ile Tyr Glu Thr Met Pro Ala Trp Glu Glu Asp Ile Thr Gly Cys Thr
    370                 375                 380

Thr Phe Glu Glu Leu Pro Gln Lys Ala Gln Asp Tyr Val Leu Arg Leu
385                 390                 395                 400

Glu Glu Leu Ser Gly Thr Arg Met Ser Tyr Ile Gly Val Gly Pro Gly
                405                 410                 415

Arg Asp Gln Thr Ile Val Arg His Asp Val Leu Asp Glu Lys
            420                 425                 430

<210> SEQ ID NO 3
<211> LENGTH: 1500
<212> TYPE: DNA
<213> ORGANISM: Unknown
<220> FEATURE:
<223> OTHER INFORMATION: purF

<400> SEQUENCE: 3
gtggtgaaca ctactttccc cagcgacgtg aatttagatg accaaggcga gcaagaaccc      60
cgcgaagagt gcggtgtctt tggcgtctgg gctcctggtg aagatgttgc gacactgacc     120
tactttggtc tgttcgcatt gcagcatcgt gggcaggaag ctgcaggtat cggcgtcggt     180
gatggagacc gcctcgttgt cttcaaagac atgggcttgg tctcgaatat tttcgatgag     240
tccattttaa attccctcca tggctccgtg ggcgtggggc atacgcgcta ctcgactgcc     300

```
ggtggcaaag agtggtcgaa tgtccagccg atgtttaata ccacctcaaa tggggtagac    360
atcgctttgt gccacaacgg caacttggtg aactaccaag aactgcgcga tgaagcagta    420
gctctgggac tttaccgaga gaatgaaaaa tccctgtcgg attccatgat catgacagct    480
ttgctggcgc acggagtcgg ggaaggcaac tctgtctttg acgccgctaa gcaactgctg    540
ccaagcatca aggcgctttt tgcttgacc tttaccgatg gcaagacctt gtacgccgcg    600
cgtgacccgc acggtgtacg ccccttggtc attggccgct ggcgcaagg ctgggttgtt    660 gcttccgaaa cctgtgcgct ggatatcgtg ggcgcacagt ttatccgtga ggtagagccc    720
ggtgaactta tctctgtcaa tgaggcagga atccacagcg aaaaattcgc tgagccgaag    780
cgccagggct gcgtctttga atacgtctac ttggcacgtc cagacaccgt gatcaaaggc    840
cgcaacgttc acgcgacgcg cgtggatatt ggtcgcgcac ttgcgaaatc tcaccctgcg    900
ccagaagctg acatggtcat ccccgtgcca gaatccggaa acccggcagc tgttggctac    960
gcccgggaat cgggcctgac atttgcgcac ggcttggtca aaaacgccta cgtgggtcga   1020
accttcattc agcccaccca gaccttgcgc cagctgggta ttcgcctcaa gctcaacccc   1080
ctgcgcgagg tcatcgaggg caagtcactc gttgttgtag atgactctat tgtccgcggc   1140
aacacccaac gcgcgctggt gcgcatgctg cgtgaagcag gcgctgctga agtgcacgtg   1200
cgcattgctt caccgccagt caaatggcct tgtttctacg gcattgactt cgcctcgcct   1260
ggtgaattga ttgctaatat caagccttct gatgatcctc aggtagtaac cgatgcagtg   1320
tgcgaagcta tcggagcaga ctctttaggg tttgtatctg tagatgagat ggttgaggca   1380
acgcaccaac ctatcaattc cttgtgtacc gcttgctttg atggcaacta cgaactcgga   1440
cttccgaccg ctaaccccaa tgctgacgct gtgcgaactt tgctcagcca aagaactga    1500
```

<210> SEQ ID NO 4
<211> LENGTH: 29
<212> TYPE: DNA
<213> ORGANISM: Artificial Sequence
<220> FEATURE:
<223> OTHER INFORMATION: primer purF g1a-1

<400> SEQUENCE: 4

```
gctctagacc actctaagac gcggccacc                                       29
```

<210> SEQ ID NO 5
<211> LENGTH: 37
<212> TYPE: DNA
<213> ORGANISM: Artificial Sequence
<220> FEATURE:
<223> OTHER INFORMATION: primer purF g1a-2

<400> SEQUENCE: 5

```
aagtagtgtt caccatgacg ctgattctac taagttt                              37
```

<210> SEQ ID NO 6
<211> LENGTH: 38
<212> TYPE: DNA
<213> ORGANISM: Artificial Sequence
<220> FEATURE:
<223> OTHER INFORMATION: primer purF g1a-3

<400> SEQUENCE: 6

```
agtagaatca gcgtcatggt gaacactact ttccccag                             38
```

<210> SEQ ID NO 7

```
<211> LENGTH: 29
<212> TYPE: DNA
<213> ORGANISM: Artificial Sequence
<220> FEATURE:
<223> OTHER INFORMATION: primer purF g1a-4

<400> SEQUENCE: 7
gctctagact gtgcgcccac gatatccag                                    29

<210> SEQ ID NO 8
<211> LENGTH: 1521
<212> TYPE: DNA
<213> ORGANISM: Unknown
<220> FEATURE:
<223> OTHER INFORMATION: guaB

<400> SEQUENCE: 8
atgaccgaaa atcgtgtttc taccggtgga gatgacccaa ataaggttgc attgcatggc     60
ttgacgtttg atgacgtgct gctgctacct gccgaatcca atgttgttcc gtcggaagta    120
gacacttcgg cgcagttcac ccgcaatact cgtttaggta ttcctttggc atcggctgcg    180
atggacacgg ttactgaggc gcgcatggct attgccatgg cacgccaggg tggcattggt    240
gtcttgcacc gcaacttgtc ctcgcaagag caggcggagc aggtcgaaat cgtcaagcgc    300
tctgagtccg gcatggtcac cgaccctgtg accgcgaatc cagacatgac tatccaggaa    360
gttgatgacc tgtgtgcacg cttccgcatc tctggtcttc ctgtggtcaa cgaagacggc    420
accttgttgg gcatttgcac caaccgcgat atgcgctttg agcgcgacta ttcccgcaag    480
gtttctgaca tcatgaccgc tatgccgctg gttgtggcaa agaaggcgt cagcaaggaa    540 gaagccctgg atctgctgtc gacgaacaag gtagaaaagc tacctatcgt tgataaaaac    600
aacaagctgt cggtctgat taccgttaaa gactttgtta agaccgaaca gttcccgaat    660
tcctccaagg atgcttcggg ccgcttgcta gtagcagcag gtattggtac cggcgaggag    720
tcttatgagc gtgcaggctt gcttgtcgat gccggcgtgg acgttctcat tgtcgactcc    780
gcacacgcgc acaataaccg cgtgctggaa atggtctcgc gcgtcaagaa tgacttcggc    840
tccaagattg atgttgtcgg cggcaacctg caacacgct cggcagcaaa ggcgatgatt    900
gaggctggcg cagacgccat caaggtgggt attggtcctg gttctatctg caccacccgt    960
gtggttgctg tgttggtgc accacagatt accgcgatca tggaagcagc taccgtggct   1020
tctgctgcgg gcgtgccttt gattgcagac ggcggcatgc agtactccgg tgacgttgct   1080
aaggctttgg ctgctggcgc ggactcggtc atgctgggct cgatgttcgc aggcaccctg   1140
gaggctcctg gtgacatcgt gattgtcggc ggcaagcagt acaagcgcta ccgcggcatg   1200
ggttcgatgg gcgctatgca aggccgtggc ctctccggcg agaagcgttc ttactccaag   1260
gaccgctact tccaggcaga tgtgcgcagc gaagataagc tggttccaga aggcgtggaa   1320
ggcaaggttc cttaccgcgg cgaaattggt cagattaccc accagattgt gggcggtttg   1380
cgcgcggcaa tgggctacac tggctccgct actattgaag agctgaagac caagcagttc   1440
gtgcgtatta ccactgctgg cttggctgag tcgcacccgc accacctgca gcaaactgta   1500
gaagctccga actaccgtta a                                             1521

<210> SEQ ID NO 9
<211> LENGTH: 29
<212> TYPE: DNA
<213> ORGANISM: Artificial Sequence
<220> FEATURE:
<223> OTHER INFORMATION: primer guaB alt-1
```

<400> SEQUENCE: 9
gctctagact acgacaacac ggtgcctaa                                        29

<210> SEQ ID NO 10
<211> LENGTH: 37
<212> TYPE: DNA
<213> ORGANISM: Artificial Sequence
<220> FEATURE:
<223> OTHER INFORMATION: primer guaB alt-2

<400> SEQUENCE: 10
cacgattttc ggtcaatacg ggtcttctcc ttcgcac                               37

<210> SEQ ID NO 11
<211> LENGTH: 36
<212> TYPE: DNA
<213> ORGANISM: Artificial Sequence
<220> FEATURE:
<223> OTHER INFORMATION: primer guaB alt-3

<400> SEQUENCE: 11
aggagaagac ccgtattgac cgaaaatcgt gtttct                                36

<210> SEQ ID NO 12
<211> LENGTH: 29
<212> TYPE: DNA
<213> ORGANISM: Artificial Sequence
<220> FEATURE:
<223> OTHER INFORMATION: primer guaB alt-4

<400> SEQUENCE: 12
gctctagaat cgacaagcaa gcctgcacg                                        29

<210> SEQ ID NO 13
<211> LENGTH: 21
<212> TYPE: DNA
<213> ORGANISM: Artificial Sequence
<220> FEATURE:
<223> OTHER INFORMATION: purA 5' primer F (temp)

<400> SEQUENCE: 13
atggctaaat acattatcac t                                                21

<210> SEQ ID NO 14
<211> LENGTH: 21
<212> TYPE: DNA
<213> ORGANISM: Artificial Sequence
<220> FEATURE:
<223> OTHER INFORMATION: purA 5' primer R (temp)

<400> SEQUENCE: 14
tgtgctggag acccctcata g                                                21

<210> SEQ ID NO 15
<211> LENGTH: 21
<212> TYPE: DNA
<213> ORGANISM: Artificial Sequence
<220> FEATURE:
<223> OTHER INFORMATION: purA error PCR primer F

<400> SEQUENCE: 15
aagggcaaag ctacagacat c                                                21

<210> SEQ ID NO 16

```
<211> LENGTH: 21
<212> TYPE: DNA
<213> ORGANISM: Artificial Sequence
<220> FEATURE:
<223> OTHER INFORMATION: purA error PCR primer R

<400> SEQUENCE: 16
ccgccgagca tgagaacccg a                                              21

<210> SEQ ID NO 17
<211> LENGTH: 21
<212> TYPE: DNA
<213> ORGANISM: Artificial Sequence
<220> FEATURE:
<223> OTHER INFORMATION: primer purA seq F

<400> SEQUENCE: 17
gacgcgtcgg aatcgccgat a                                              21

<210> SEQ ID NO 18
<211> LENGTH: 21
<212> TYPE: DNA
<213> ORGANISM: Artificial Sequence
<220> FEATURE:
<223> OTHER INFORMATION: primer purA seq R

<400> SEQUENCE: 18
ccgccgagca tgagaacccg a                                              21

<210> SEQ ID NO 19
<211> LENGTH: 27
<212> TYPE: DNA
<213> ORGANISM: Artificial Sequence
<220> FEATURE:
<223> OTHER INFORMATION: primer purA(G85S) F

<400> SEQUENCE: 19
gctctagatg ccggcatttt tcgaagc                                        27

<210> SEQ ID NO 20
<211> LENGTH: 29
<212> TYPE: DNA
<213> ORGANISM: Artificial Sequence
<220> FEATURE:
<223> OTHER INFORMATION: primer purA(G85S) R

<400> SEQUENCE: 20
gctctagaaa gtagtcggta aagccgttg                                      29

<210> SEQ ID NO 21
<211> LENGTH: 36
<212> TYPE: DNA
<213> ORGANISM: Artificial Sequence
<220> FEATURE:
<223> OTHER INFORMATION: primer purA(G85A) F

<400> SEQUENCE: 21
ctttgaggaa attgaagctc tcgaagcccg cggcgc                              36

<210> SEQ ID NO 22
<211> LENGTH: 36
<212> TYPE: DNA
<213> ORGANISM: Artificial Sequence
<220> FEATURE:
<223> OTHER INFORMATION: primer purA(G85A) R

<400> SEQUENCE: 22
```

```
gcgccgcggg cttcgagagc ttcaatttcc tcaaag                       36
```

<210> SEQ ID NO 23
<211> LENGTH: 36
<212> TYPE: DNA
<213> ORGANISM: Artificial Sequence
<220> FEATURE:
<223> OTHER INFORMATION: primer purA(G85V) F

<400> SEQUENCE: 23

```
ctttgaggaa attgaagtcc tcgaagcccg cggcgc                       36
```

<210> SEQ ID NO 24
<211> LENGTH: 36
<212> TYPE: DNA
<213> ORGANISM: Artificial Sequence
<220> FEATURE:
<223> OTHER INFORMATION: primer purA(G85V) R

<400> SEQUENCE: 24

```
gcgccgcggg cttcgaggac ttcaatttcc tcaaag                       36
```

<210> SEQ ID NO 25
<211> LENGTH: 36
<212> TYPE: DNA
<213> ORGANISM: Artificial Sequence
<220> FEATURE:
<223> OTHER INFORMATION: primer purA(G85L) F

<400> SEQUENCE: 25

```
ctttgaggaa attgaactgc tcgaagcccg cggcgc                       36
```

<210> SEQ ID NO 26
<211> LENGTH: 36
<212> TYPE: DNA
<213> ORGANISM: Artificial Sequence
<220> FEATURE:
<223> OTHER INFORMATION: primer purA(G85L) R

<400> SEQUENCE: 26

```
gcgccgcggg cttcgagcag ttcaatttcc tcaaag                       36
```

<210> SEQ ID NO 27
<211> LENGTH: 36
<212> TYPE: DNA
<213> ORGANISM: Artificial Sequence
<220> FEATURE:
<223> OTHER INFORMATION: primer purA(G85M) F

<400> SEQUENCE: 27

```
ctttgaggaa attgaaatgc tcgaagcccg cggcgc                       36
```

<210> SEQ ID NO 28
<211> LENGTH: 36
<212> TYPE: DNA
<213> ORGANISM: Artificial Sequence
<220> FEATURE:
<223> OTHER INFORMATION: primer purA(G85M) R

<400> SEQUENCE: 28

```
gcgccgcggg cttcgagcat ttcaatttcc tcaaag                       36
```

<210> SEQ ID NO 29
<211> LENGTH: 36
<212> TYPE: DNA

```
<213> ORGANISM: Artificial Sequence
<220> FEATURE:
<223> OTHER INFORMATION: primer purA(G85I) F

<400> SEQUENCE: 29
ctttgaggaa attgaaatcc tcgaagcccg cggcgc                               36

<210> SEQ ID NO 30
<211> LENGTH: 36
<212> TYPE: DNA
<213> ORGANISM: Artificial Sequence
<220> FEATURE:
<223> OTHER INFORMATION: primer purA(G85I) R

<400> SEQUENCE: 30
gcgccgcggg cttcgaggat ttcaatttcc tcaaag                               36

<210> SEQ ID NO 31
<211> LENGTH: 36
<212> TYPE: DNA
<213> ORGANISM: Artificial Sequence
<220> FEATURE:
<223> OTHER INFORMATION: primer purA(G85T) F

<400> SEQUENCE: 31
ctttgaggaa attgaaactc tcgaagcccg cggcgc                               36

<210> SEQ ID NO 32
<211> LENGTH: 36
<212> TYPE: DNA
<213> ORGANISM: Artificial Sequence
<220> FEATURE:
<223> OTHER INFORMATION: primer purA(G85T) R

<400> SEQUENCE: 32
gcgccgcggg cttcgagagt ttcaatttcc tcaaag                               36

<210> SEQ ID NO 33
<211> LENGTH: 36
<212> TYPE: DNA
<213> ORGANISM: Artificial Sequence
<220> FEATURE:
<223> OTHER INFORMATION: primer purA(G85N) F

<400> SEQUENCE: 33
ctttgaggaa attgaaaacc tcgaagcccg cggcgc                               36

<210> SEQ ID NO 34
<211> LENGTH: 36
<212> TYPE: DNA
<213> ORGANISM: Artificial Sequence
<220> FEATURE:
<223> OTHER INFORMATION: primer purA(G85N) R

<400> SEQUENCE: 34
gcgccgcggg cttcgaggtt ttcaatttcc tcaaag                               36

<210> SEQ ID NO 35
<211> LENGTH: 36
<212> TYPE: DNA
<213> ORGANISM: Artificial Sequence
<220> FEATURE:
<223> OTHER INFORMATION: primer purA(G85Q) F

<400> SEQUENCE: 35
ctttgaggaa attgaacagc tcgaagcccg cggcgc                               36
```

<210> SEQ ID NO 36
<211> LENGTH: 36
<212> TYPE: DNA
<213> ORGANISM: Artificial Sequence
<220> FEATURE:
<223> OTHER INFORMATION: primer purA(G85Q) R

<400> SEQUENCE: 36
gcgccgcggg cttcgagctg ttcaatttcc tcaaag         36

<210> SEQ ID NO 37
<211> LENGTH: 36
<212> TYPE: DNA
<213> ORGANISM: Artificial Sequence
<220> FEATURE:
<223> OTHER INFORMATION: primer purA(G85C) F

<400> SEQUENCE: 37
ctttgaggaa attgaatgcc tcgaagcccg cggcgc         36

<210> SEQ ID NO 38
<211> LENGTH: 36
<212> TYPE: DNA
<213> ORGANISM: Artificial Sequence
<220> FEATURE:
<223> OTHER INFORMATION: primer purA(G85C) R

<400> SEQUENCE: 38
gcgccgcggg cttcgaggca ttcaatttcc tcaaag         36

<210> SEQ ID NO 39
<211> LENGTH: 36
<212> TYPE: DNA
<213> ORGANISM: Artificial Sequence
<220> FEATURE:
<223> OTHER INFORMATION: primer purA(G85P) F

<400> SEQUENCE: 39
ctttgaggaa attgaaccac tcgaagcccg cggcgc         36

<210> SEQ ID NO 40
<211> LENGTH: 36
<212> TYPE: DNA
<213> ORGANISM: Artificial Sequence
<220> FEATURE:
<223> OTHER INFORMATION: primer purA(G85P) R

<400> SEQUENCE: 40
gcgccgcggg cttcgagtgg ttcaatttcc tcaaag         36

<210> SEQ ID NO 41
<211> LENGTH: 36
<212> TYPE: DNA
<213> ORGANISM: Artificial Sequence
<220> FEATURE:
<223> OTHER INFORMATION: primer purA(G85Y) F

<400> SEQUENCE: 41
ctttgaggaa attgaatacc tcgaagcccg cggcgc         36

<210> SEQ ID NO 42
<211> LENGTH: 36
<212> TYPE: DNA
<213> ORGANISM: Artificial Sequence
<220> FEATURE:

```
<223> OTHER INFORMATION: primer purA(G85Y) R

<400> SEQUENCE: 42
gcgccgcggg cttcgaggta ttcaatttcc tcaaag                              36

<210> SEQ ID NO 43
<211> LENGTH: 36
<212> TYPE: DNA
<213> ORGANISM: Artificial Sequence
<220> FEATURE:
<223> OTHER INFORMATION: primer purA(G85W) F

<400> SEQUENCE: 43
ctttgaggaa attgaatggc tcgaagcccg cggcgc                              36

<210> SEQ ID NO 44
<211> LENGTH: 36
<212> TYPE: DNA
<213> ORGANISM: Artificial Sequence
<220> FEATURE:
<223> OTHER INFORMATION: primer purA(G85W) R

<400> SEQUENCE: 44
gcgccgcggg cttcgagcca ttcaatttcc tcaaag                              36

<210> SEQ ID NO 45
<211> LENGTH: 36
<212> TYPE: DNA
<213> ORGANISM: Artificial Sequence
<220> FEATURE:
<223> OTHER INFORMATION: primer purA(G85K) F

<400> SEQUENCE: 45
ctttgaggaa attgaaaagc tcgaagcccg cggcgc                              36

<210> SEQ ID NO 46
<211> LENGTH: 36
<212> TYPE: DNA
<213> ORGANISM: Artificial Sequence
<220> FEATURE:
<223> OTHER INFORMATION: primer purA(G85K) R

<400> SEQUENCE: 46
gcgccgcggg cttcgagctt ttcaatttcc tcaaag                              36

<210> SEQ ID NO 47
<211> LENGTH: 36
<212> TYPE: DNA
<213> ORGANISM: Artificial Sequence
<220> FEATURE:
<223> OTHER INFORMATION: primer purA(G85R) F

<400> SEQUENCE: 47
ctttgaggaa attgaacgcc tcgaagcccg cggcgc                              36

<210> SEQ ID NO 48
<211> LENGTH: 36
<212> TYPE: DNA
<213> ORGANISM: Artificial Sequence
<220> FEATURE:
<223> OTHER INFORMATION: primer purA(G85R) R

<400> SEQUENCE: 48
gcgccgcggg cttcgaggcg ttcaatttcc tcaaag                              36
```

<210> SEQ ID NO 49
<211> LENGTH: 36
<212> TYPE: DNA
<213> ORGANISM: Artificial Sequence
<220> FEATURE:
<223> OTHER INFORMATION: primer purA(G85H) F

<400> SEQUENCE: 49
ctttgaggaa attgaacacc tcgaagcccg cggcgc                36

<210> SEQ ID NO 50
<211> LENGTH: 36
<212> TYPE: DNA
<213> ORGANISM: Artificial Sequence
<220> FEATURE:
<223> OTHER INFORMATION: primer purA(G85H) R

<400> SEQUENCE: 50
gcgccgcggg cttcgaggtg ttcaatttcc tcaaag                36

<210> SEQ ID NO 51
<211> LENGTH: 36
<212> TYPE: DNA
<213> ORGANISM: Artificial Sequence
<220> FEATURE:
<223> OTHER INFORMATION: primer purA(G85D) F

<400> SEQUENCE: 51
ctttgaggaa attgaagatc tcgaagcccg cggcgc                36

<210> SEQ ID NO 52
<211> LENGTH: 36
<212> TYPE: DNA
<213> ORGANISM: Artificial Sequence
<220> FEATURE:
<223> OTHER INFORMATION: primer purA(G85D) R

<400> SEQUENCE: 52
gcgccgcggg cttcgagatc ttcaatttcc tcaaag                36

<210> SEQ ID NO 53
<211> LENGTH: 36
<212> TYPE: DNA
<213> ORGANISM: Artificial Sequence
<220> FEATURE:
<223> OTHER INFORMATION: primer purA(G85E) F

<400> SEQUENCE: 53
ctttgaggaa attgaagaac tcgaagcccg cggcgc                36

<210> SEQ ID NO 54
<211> LENGTH: 36
<212> TYPE: DNA
<213> ORGANISM: Artificial Sequence
<220> FEATURE:
<223> OTHER INFORMATION: primer purA(G85E) R

<400> SEQUENCE: 54
gcgccgcggg cttcgagttc ttcaatttcc tcaaag                36

<210> SEQ ID NO 55
<211> LENGTH: 27
<212> TYPE: DNA
<213> ORGANISM: Artificial Sequence
<220> FEATURE:
<223> OTHER INFORMATION: purA(G85S) F -continued

```
<400> SEQUENCE: 55
gctctagatg ccggcatttt tcgaagc                                              27

<210> SEQ ID NO 56
<211> LENGTH: 29
<212> TYPE: DNA
<213> ORGANISM: Artificial Sequence
<220> FEATURE:
<223> OTHER INFORMATION: purA(G85S) R

<400> SEQUENCE: 56
gctctagaaa gtagtcggta aagccgttg                                            29
```